(12) United States Patent
Takagi et al.

(10) Patent No.: US 11,744,483 B2
(45) Date of Patent: Sep. 5, 2023

(54) PROGRAM, COMPUTER APPARATUS, AND SYSTEM FOR ASSESSING MUSCLE TONE, AND MUSCLE TONE ASSESSMENT METHOD

(71) Applicant: Rika Takagi, Aichi (JP)

(72) Inventors: Rika Takagi, Aichi (JP); Hisayoshi Yoshitake, Aichi (JP); Toshimitsu Ishizuka, Kanagawa (JP)

(73) Assignee: Rika Takagi, Aichi (JP)

( * ) Notice: Subject to any disclaimer, the term of this patent is extended or adjusted under 35 U.S.C. 154(b) by 92 days.

(21) Appl. No.: 16/627,490

(22) PCT Filed: Jul. 7, 2017

(86) PCT No.: PCT/JP2017/025043
§ 371 (c)(1),
(2) Date: Dec. 30, 2019

(87) PCT Pub. No.: WO2019/008772
PCT Pub. Date: Jan. 10, 2019

(65) Prior Publication Data
US 2020/0163589 A1 May 28, 2020

(51) Int. Cl.
*A61B 5/11* (2006.01)
*G16H 30/00* (2018.01)
*A61B 5/00* (2006.01)

(52) U.S. Cl.
CPC .......... *A61B 5/1107* (2013.01); *A61B 5/0077* (2013.01); *A61B 5/1128* (2013.01);
(Continued)

(58) Field of Classification Search
CPC ..... A61B 5/1107; A61B 5/107; A61B 5/1071; A61B 5/1072; A61B 5/1075;
(Continued)

(56) References Cited

U.S. PATENT DOCUMENTS 9,788,759 B2 * 10/2017 Ferrantelli ........... A61B 5/1072
2005/0182341 A1 8/2005 Katayama et al.
(Continued)

FOREIGN PATENT DOCUMENTS

JP 2005-224452 8/2005
JP 2012-081089 4/2012
(Continued)

OTHER PUBLICATIONS

Saenz-de-Urturi, et al. "Kinect-based virtual game for the elderly that detects incorrect body postures in real time." Sensors 16.5 (2016): 704. (Year: 2016).*
(Continued)

*Primary Examiner* — David J. McCrosky
(74) *Attorney, Agent, or Firm* — GREENBLUM & BERNSTEIN, P.L.C.

(57) ABSTRACT

The present invention provides a program capable of assessing the muscle tone of the exerciser based on the captured images of the posture of the exerciser. The above object is achieved by a program causing a computer apparatus to execute assessment of muscle tone of a client, the program causing the computer apparatus to function as: an image capturer that captures an image of a posture of the client in a steady state and/or an image of a posture of the client in a moving state; and an assessor that assesses the muscle tone of the client based on a position of a prescribed body site of the client, an inclination of the prescribed body site of the client, and/or positional relationships among a plurality of prescribed body sites in the image captured by the image capturer.

7 Claims, 8 Drawing Sheets

(52) U.S. Cl.
CPC ............ *A61B 5/4519* (2013.01); *A61B 5/702* (2013.01); *G16H 30/00* (2018.01)

(58) Field of Classification Search
CPC ... A61B 5/0077; A61B 5/1114; A61B 5/1116; A61B 5/1126; A61B 5/1127; A61B 5/1128; A61B 5/4519; A61B 5/702; A61B 5/4561; G16H 30/00
See application file for complete search history.

(56) References Cited

U.S. PATENT DOCUMENTS

| | | | |
|---|---|---|---|
| 2012/0086793 A1 | 4/2012 | Anabuki | |
| 2014/0330186 A1* | 11/2014 | Hyde | A61B 5/1118 602/19 |

FOREIGN PATENT DOCUMENTS

| | | |
|---|---|---|
| JP | 2012-139480 | 7/2012 |
| JP | 2017-047105 | 3/2017 |

OTHER PUBLICATIONS

Eguíluz, et al. "Use of a time-of-flight camera with an omek beckon™ framework to analyze, evaluate and correct in real time the verticality of multiple sclerosis patients during exercise." International journal of environmental research and public health 10.11 (2013): 580 (Year: 2013).*

International Search Report issued in International Patent Application No. PCT/JP2017/025043, dated Oct. 3, 2017 with an English translation thereof.

Official Communication Received in Japanese Patent Application No. JP2021-014679, dated Jan. 11, 2022 with an English translation thereof.

* cited by examiner

PROGRAM, COMPUTER APPARATUS, AND SYSTEM FOR ASSESSING MUSCLE TONE, AND MUSCLE TONE ASSESSMENT METHOD

TECHNICAL FIELD

The present invention relates to a program, a computer apparatus, and a system for assessing muscle tone and to a muscle tone assessment method.

BACKGROUND ART

In order for persons to maintain the physical condition, it is important to do moderate exercise on a regular basis. Recently, an increasing number of people do exercise by utilizing training facilities in order to increase one's motor functions. Further, in therapeutic facilities such as an osteopathic clinic, a chiropractic clinic, and a rehabilitation facility, so-called exercise therapy is performed with which symptoms of a patient can be lightened or cured or the functions can be recovered by encouraging the patient to do various kinds of exercise.

In order to increase the effect achieved by the exercise, it is necessary to determine the exercise menu by fully considering the state of the body of the exerciser. For example, when the state of the body of the exerciser is not in a suitable state for performing even a generally-recommended exercise menu, muscles that are not supposed to be used may be used or excessive load may be imposed upon joints and soft tissues in the periphery of the joints when performing the exercise menu, which may rather cause damages or general malaise.

In order to overcome such a problem, for example, Patent Literature 1 discloses a system which extracts specific site images showing a plurality of specific sites from captured images of a standing position of an exerciser, analyzes the posture of each of the specific sites based on the specific site images, and provides an exercise menu corresponding to the posture of each of the specific sites to the exerciser.

CITATION LIST

Patent Literature

Patent Literature 1: JP 2017-47105 A

SUMMARY OF INVENTION

Technical Problem

Incidentally, in order to provide the exercise menu which is more effective for the exerciser thereof and in which the probability of causing damages or general malaise is more decreased, it is preferable to grasp the muscle tone of the exerciser. For example, when the positions of muscles in a hypertonic (shortened) state (also referred to as "tensed muscles" hereinafter) and the positions of muscles in a hypotonic (relaxed or weakened) state (also referred to as "relaxed muscles" hereinafter) become apparent, it is possible to provide the exercise menu that can properly work on each of the muscles, that is, the exercise menu more suited for the exerciser.

However, the system disclosed in Patent Literature 1 is not designed to provide the exercise menu upon grasping the muscle tone of the user. In order to provide the exercise menu more suited for the exerciser, it is desired to be able to grasp the muscle state of the user with a simple method.

The present invention is designed in view of the aforementioned problem. That is, it is the object of the present invention to provide a program capable of assessing the muscle tone of the exerciser based on the captured images of the posture of the exerciser.

Solution to Problem

The present invention is summarized as follows.

[1] A program causing a computer apparatus to execute assessment of muscle tone of a client, the program causing the computer apparatus to function as: an image capturer that captures an image of a posture of the client in a steady state and/or an image of a posture of the client in a moving state; and an assessor that assesses the muscle tone of the client based on a position of a prescribed body site of the client, an inclination of the prescribed body site of the client, and/or positional relationships among a plurality of prescribed body sites in the image captured by the image capturer.

[2] The program according to above [1], further causing the computer apparatus to function as an object generator that generates a plurality of objects for visualizing the positions and/or the inclinations of each of the prescribed body sites of the client, wherein the assessor assesses the muscle tone of the client based on positions of the objects, inclinations of the objects, and positional relationships among the plurality of objects.

[3] The program according to above [2], wherein the assessor further assesses the muscle tone of the client based on a positional relationship between the objects neighboring to each other.

[4] The program according to any one of above [1] to [3], wherein the assessor assesses whether the muscle at a prescribed site is in a hypotonic state or in a hypertonic state, the program further causing the computer apparatus to function as a displayer that displays the position of the muscle in the hypotonic state and/or the muscle in the hypertonic state in a prescribed mode.

[5] The program according to any one of above [1] to [4], further causing the computer apparatus to function as an exercise determiner that determines the exercise to be performed by the client based on the assessment made by the assessor.

[6] A computer apparatus executing assessment of muscle tone of a client, including: an image capturer that captures an image of a posture of the client in a steady state and/or an image of a posture of the client in a moving state; and an assessor that assesses the muscle tone of the client based on a position of a prescribed body site, an inclination of the prescribed body site, and/or positional relationships among a plurality of prescribed body sites in the image captured by the image capturer.

[7] A muscle tone assessment method for assessing muscle tone of a client, including: a step of capturing an image of a posture of the client in a steady state and/or an image of a posture of the client in a moving state by using an image capturing apparatus; and a step of assessing the muscle tone of the client based on a position of a prescribed body site of the client, an inclination of the prescribed body site of the client, and/or positional relationships among a plurality of prescribed body sites in the image captured in the step of capturing the image.

[8] A system assessing muscle tone of a client implemented by a computer apparatus and a server apparatus connectable to the computer apparatus via communication, the system including: an image capturer that captures an image of a posture of the client in a steady state and/or an image of a posture of the client in a moving state; and an assessor that assesses the muscle tone of the client based on a position of a prescribed body site, an inclination of the prescribed body site, and/or positional relationships among a plurality of prescribed body sites in the image captured by the image capturer.

Advantageous Effects of Invention

With the present invention, it is possible to assess the muscle tone of the exerciser based on the captured images of the posture of the exerciser.

DESCRIPTION OF EMBODIMENTS

Figure 1:
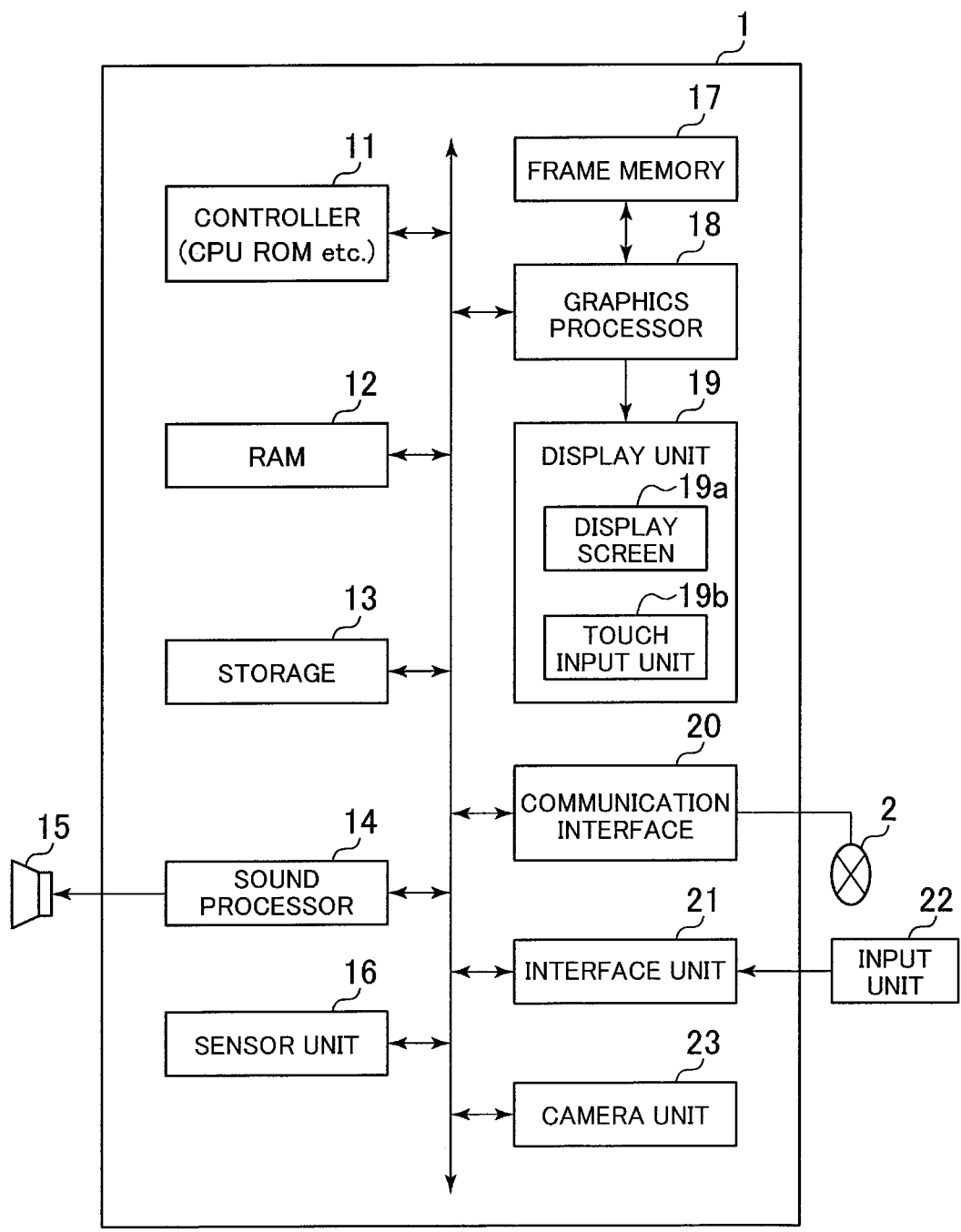
FIG. 1 is a block diagram illustrating a configuration of a computer apparatus 1 corresponding to at least one of the embodiments of the present invention.

While embodiments of the present invention will be described with reference to the accompanying drawings and the like hereinafter, the present invention is not limited to the following embodiments without departing from the purpose of the present invention. In the drawings, different numeral signs may be applied even to the same sites of human bodies. Further, the sequential order of each processing constituting flowcharts described in the Description is a random order within a range where there is no confliction or inconsistency generated in the processing contents.

In the Description, a "client" means a person who performs exercise, and examples thereof may be users of training facilities, sports enthusiasts, athletes, and patients performing exercise therapies. Further, a "trainer" means a person who gives instructions and advices regarding the exercise for the client, and examples thereof may be instructors of training facilities, sport trainers, coaches, judo therapists, and physical therapists. Furthermore, an "image" may be a still image or a video.

First Embodiment

First, outline of the first embodiment of the present invention will be described. Hereinafter, a program causing a computer apparatus to execute assessment of the muscle tone of a client will be described as the first embodiment.

With the computer apparatus capable of executing the program according to the first embodiment, it is possible to capture images of the posture of the client by a trainer or by the client himself, for example, and to assess the muscle tone of the client based on the position of a prescribed body site of the client, an inclination the prescribed body site of the client, and/or positional relationships among a plurality of prescribed body sites in the captured image. Further, it is possible to provide the exercise menu suited for the client based on the assessment result of the muscle tone of the client.

FIG. 1 is a block diagram illustrating a configuration of a computer apparatus 1 corresponding to at least one of the embodiments of the present invention. The computer apparatus 1 includes at least a controller 11, a RAM (Random Access Memory) 12, a storage 13, a sound processor 14, a sensor unit 16, a graphics processor 18, a display unit 19, a communication interface 20, an interface unit 21, and a camera unit 23, and each of those is connected via an internal bus.

The computer apparatus 1 is a terminal to be operated by a client. While not limited thereto, examples of the computer apparatus 1 may be a personal computer, a smartphone, a tablet terminal, a mobile phone, a PDA, and a server apparatus. It is preferable for the computer apparatus 1 to be connectable for communication with other computer apparatuses via the communication network 2.

As examples of the communication network 2, there may be various kinds of wired or wireless known communication networks such as the Internet, wired or wireless public telephone network, wired or wireless LAN, and a dedicated line.

The controller 11 is configured with a CPU (Central Processor) and a ROM (Read Only Memory), and includes an internal timer for clocking the time. The controller 11 executes programs stored in the storage 13 and controls the computer apparatus 1. The RAM 12 is a work area of the controller 11. The storage 13 is a memory area for saving the programs and data.

The controller 11 reads out the program and data from the RAM 12 and performs processing. The controller 11 processes the program and the data loaded on the RAM 12 to output an instruction to output sound to the sound processor 14 and to output an image drawing command to the graphics processor 18.

The sound processor 14 is connected to a sound output apparatus 15 that is a speaker. When the controller 11 outputs an instruction of sound output to the sound processor 14, the sound processor 14 outputs a sound signal to the sound output apparatus 15. It is preferable to output instructions regarding the posture of the client and exercise contents and feedback regarding the exercise, for example, from the sound output apparatus 15 with voice.

The sensor unit 16 includes at least one or more sensor selected from a group consisting of a depth sensor, an accelerometer, a gyro sensor, a GPS sensor, a fingerprint authentication sensor, a proximity sensor, a magnetic sensor, a luminance sensor, a GPS sensor, and a barometric pressure sensor. In view of monitoring in detail the state of the exercise performed by the client, it is preferable for the sensor unit 16 to include the depth sensor, for example. Note that, in order to monitor in detail the state of the exercise performed by the client, an external apparatus such as a motion capture apparatus, a pressure sensor, electromyography, or an ultrasonic measurement device may be used, and the information from the external apparatus may be received at the computer apparatus 1.

The graphics processor 18 is connected to the display unit 19. The display unit 19 includes a display screen 19*a* and a touch input unit 19*b*. When the controller 11 outputs an image drawing command to the graphics processor 18, the graphics processor 18 develops an image on a frame memory (frame buffer) 17, and outputs a video signal for displaying the image on the display screen 19*a*. The touch input unit 19*b* receives operation input of the client, senses a pressure on the touch input unit 19*b* applied by a finger, a stylus, or the like and shift of the position of the finger or the like, and detects a change and the like of the coordinate position. The display screen 19*a* and the touch input unit 19*b* may also be configured integrally like a touch panel, for example.

The graphics processor 18 executes drawing of a single image by a frame unit. One frame time of the image is $\frac{1}{30}$ seconds, for example. The graphics processor 18 has a role of dispersing the load on the controller 11 by undertaking a part of calculation processing regarding drawing the image that is used to be carried out by the controller 11 alone.

The communication interface 20 is capable of connecting to the communication network 2 wirelessly or with wire, and capable of transmitting/receiving data via the communication network 2. The data received via the communication network 2 is loaded on the RAM 12, and calculation processing is performed by the controller 11.

To the interface unit 21, an input unit 22 (for example, a mouse or a keyboard) can be connected. Input information inputted by the client through the input unit 22 is stored in the RAM 12, and the controller 11 executes various kinds of calculation processing based on the input information. Alternatively, it is also possible to connect a storage medium reader to the interface unit 21, and load the program, the data, and the like from an external memory or the like. Further, it is also possible to use the display unit 19 provided with a touch panel as the input unit 22.

The camera unit 23 is for capturing images of the client, and captures the postures of the client in a steady state and/or moving state and the state where the client is performing the exercise, for example. The image captured by the camera unit 23 is outputted to the graphics processor 18. Note that the camera unit 23 may not be provided to the computer apparatus 1. For example, the captured images of the client may be acquired by fetching images captured by an external image capturing apparatus.

Next, functions of the computer apparatus corresponding to at least one of the embodiments of the present invention will be described. The computer apparatus 1 includes an image capturing function, an object generating function, an input receiving function, a posture assessing function, a muscle tone assessing function, an exercise menu determining function, a display function, and a storing function, for example.

The image capturing function has a function of capturing images of the client. The images of the posture of the client in a steady state and/or the posture of the client in a moving state are captured by the image capturing function. Note that, instead of the image capturing function, it is also possible to be configured to be capable of fetching the images captured by an external image capturing apparatus to the computer apparatus 1.

The object generating function has a function of generating a prescribed object corresponding to a prescribed body site of the client based on the image captured by the image capturing function. The object generating function makes it possible to easily visualize positions and/or inclinations of each of the prescribed body sites of the client. The generated object can be displayed on the display screen 19*a* and the display screen 49*a*. When the captured image is a video, for example, an object may be generated for each of frames constituting the video or an object may be generated only for a prescribed frame constituting the video, such as a still image acquired by temporarily stopping the video.

The input receiving function has a function of receiving operation input made on the computer apparatus 1 by the trainer or the client. The operation input may be done via an input apparatus such as a touch panel or a keyboard provided to the computer apparatus 1, for example. The input receiving function receives input for correcting the positions, inclinations, and the like of the objects generated by the object generating function, for example. By having such configuration with which the trainer and the like can correct the positions, inclinations, and the like of the objects, the muscle tone of the client can be more accurately surmised. Further, the input receiving function is preferable to be able to input information regarding the client such as the chief complaint of the client, the purpose of exercise, and the like.

The posture assessing function has a function of assessing the posture of the client in a steady state and/or a moving state. The posture assessing function can assess the posture of the client based on the captured image of the posture of the client in a steady state and/or a moving state or an object generated by the object generation function, for example. The posture assessing function is preferable to have a function of automatically calculating which pattern the posture of the client belongs to among a plurality of posture patterns exhibiting differences with respect to an ideal posture that is set in advance.

The muscle tone assessing function has a function of surmising and deducing the muscle tone in a prescribed site of the client. The muscle tone assessing function surmises the muscle tone based on the position of the prescribed body site of the client, an inclination of the prescribed body site of the client, and/or the positional relationships among a plurality of prescribed body sites. The muscle tone assessing function can surmise whether the muscle tone of a prescribed site of the client is in a tensed (shortened) hypertonic state, in a relaxed (weakened) hypotonic state, or in a normal state.

In view of increasing the accuracy, for example, it is preferable for the muscle tone assessing function to surmise and deduce the muscle tone based on the objects generated by the object generating function, and more preferable to surmise and deduce the muscle tone based on the positions of each of the objects, inclinations of each of the objects, and/or the positional relationships among a plurality of objects. Especially, by considering the positional relationship among a plurality of objects, it becomes possible to surmise the muscle tone more accurately than the case where the muscle tone is surmised by paying attention to only one body site.

The exercise menu determining function has a function of determining the exercise menu to be performed by the client based on the surmised result of the muscle tone acquired by the muscle tone assessing function. It is preferable for the exercise menu determining function to determine the exercise menu based further on the information regarding the client such as the chief complaint of the client and the purpose of exercise. Note that the exercise menu determining function may be the function that determines candidates of the exercise menu to be performed by the client. When configured as such, the trainer or the client may be allowed to select the exercise menu to be performed by the client from the candidates of the exercise menu, for example.

The display function has a function of displaying images captured by the image capturing function, objects generated by the object generating function, and various kinds of information such as information regarding the posture assessment, information regarding the muscle tone surmised by the muscle tone assessing function, information regarding exercise menus determined by the exercise menu determining function, and the like in a mode that can be recognized by the client and the trainer.

The storing function has a function of storing, for example, the information regarding the surmised result of the muscle tone acquired by the muscle tone assessing function and the information regarding the exercise menu performed by the client, which is the exercise menu determined by the exercise menu determining function. Further, the storing function is preferable to store the information regarding the surmised result of the muscle tone and the information regarding the exercise menu performed by the client by associating with the date or the time and date on which those are performed. Furthermore, it is preferable for the storing function to be able to store the information and the like received via input of the input receiving function, for example, and also preferable to be able to store such information by associating with the date or the time and date on which the information is inputted or the information is transmitted.

Figure 2:
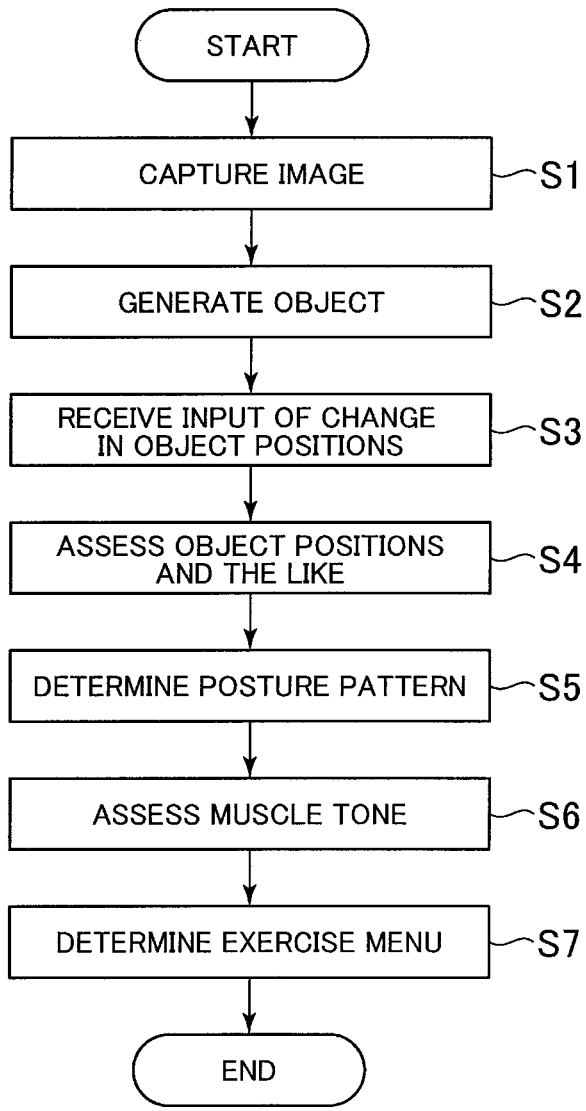
FIG. 2 is a flowchart of the program execution processing corresponding to at least one of the embodiments of the present invention.

Next, program execution processing according to the embodiment will be described. FIG. 2 is a flowchart of the program execution processing corresponding to at least one of the embodiments of the present invention.

The computer apparatus 1 captures the image of the posture of the client in a steady state and/or the posture of the client in a moving state (step S1). As the steady state, for example, a state keeping a posture such as a standing position, a bent-forward position while standing, a bent-backward position while standing, a rotating position while standing, a sitting position, a knee-standing position, or the like is preferable. However, the steady state is not limited to those. Further, as the moving state, for example, it is preferable to be a state where a multi-joint exercise is performed with no shift in the base of support. Specifically, overhead squat, single-leg squat, squat and hip rotation, bending forward while standing, bending backward while standing, rotating while standing, shoulder abduction, shoulder horizontal adduction, or the like is preferable. However, the moving state is not limited to those. In view of increasing the easiness and accuracy of the assessment of the muscle tone, it is preferable to have the client perform at least one out of the standing position, the overhead squat, and the squat and hip rotation in step S1, and to capture the image of the posture of the client.

Further, the posture in step S1 may be the posture in a state where the client is on a prescribed exercise aid. As the exercise aid, it is preferable to use a substantially columnar aid or a substantially semicolumnar aid. Specifically, examples thereof may be StretchPole® and StretchPole® HALF CUT manufactured by LPN.Corporation. When such exercise aids are used in step S1, it is preferable to capture images of the postures in a state where a spine position is kept on the exercise aid, in a state when performing axial rotation while taking a spine position on the exercise aid, and in a state when elevating arms and legs by taking a spine position or a prone position on the exercise aid, for example.

Further, as the exercise aid, it is preferable to have an abdomen support part that supports the abdomen of the client and to have a protruded part provided on a side opposing to the side of the abdomen support part supporting the abdomen for enabling the exercise of moving laterally while supporting the abdomen, and preferable to be able to support the abdomen of the client when the client takes a prone position and to enable the client to move limbs in that state. Specifically, examples thereof may be SWING STRETCH® and the like manufactured by LPN.Corporation. When such exercise aid is used in step S1, it is preferable to capture an image of the posture when lifting a hand and a leg at diagonal positions from the floor, for example, from a state where both elbows and both knees are placed on the floor by while taking a prone position on the exercise aid, for example.

Further, in step S1, the images are captured from the front of the client, from the side, or from the two directions that are from the front and the side depending on the contents of a steady state and/or a moving state to be performed by the client. For example, it is preferable to capture the images from the two directions that are from the front and the side in a case of a standing position and a case of overhead squat, while it is preferable to capture the images from the front in a case of squat and hip rotation. By changing the directions for capturing the images depending on the contents to be performed by the client, a more accurate assessment of the muscle tone can be achieved.

Then, the computer apparatus 1 generates and displays prescribed objects corresponding to each of the prescribed sites of the body of the client based on the image captured in step S1 (step S2). It is preferable to display the generated objects integrally with the image captured in step S1 in a superimposed manner.

Then, when the objects displayed in step S2 are not displayed at positions fully corresponding to the prescribed sites of the body of the client, the computer apparatus 1 receives input for changing the object positions from the trainer or the client (step S3).

Figure 3A:
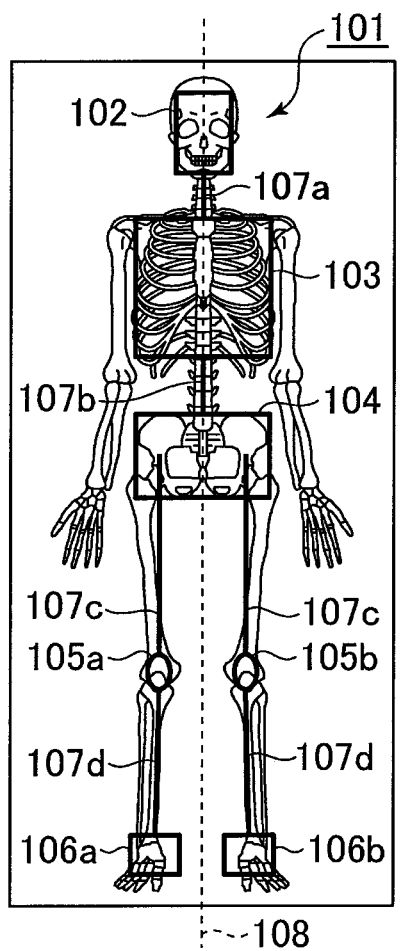
FIG. 3A and 3B are schematic views regarding an object generating method corresponding to at least one of the embodiments of the present invention.
Figure 3B:
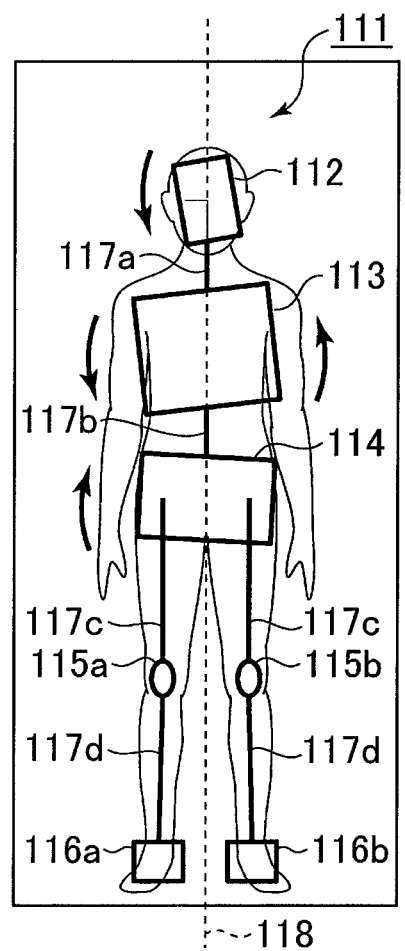

Here, by using FIGS. 3A and 3B, there is described an example of the object generating method in a case of using an image of the posture of the client captured from the front (image of frontal direction). FIG. 3 are schematic views regarding an object generating method corresponding to at least one of the embodiments of the present invention. FIG. 3A shows, by using a human skeleton chart 101, an example of the object generating method when using an image of a state captured from the front in which a client stands upright at a prescribed position such that each of the second toes of both feet faces the front while being parallel to each other, and looks straight at a designated article placed at a level of eyesight (standing position).

On the human skeleton chart 101, shown are a head object 102, a thorax object 103, a pelvis object 104, knee objects 105, and foot objects 306, which correspond to prescribed sites of the human skeleton chart. Further, a plurality of connecting lines 107 connecting each of the objects and a centroidal line 108 are shown on the human skeleton chart 301.

The head object 102 is preferable to be formed by taking a line connecting the positions of the right and left external acoustic openings as a lateral reference line and a facial median line connecting the position of the middle of the forehead and the position of the nasal groove as a longitudinal reference line, and by translating each of the reference lines to fit the outer rim of the skull, for example. The thorax object 103 is preferable to be formed by taking a line connecting the positions of the right and left acromial processes as well as a line connecting the positions of the right and left costal arches as lateral lines, respectively, and a line connecting the position of the jugular notch of manubrium of sternum and the position of the xiphoid process as a longitudinal reference line, and by translating the longitudinal reference line to fit the outer rim of the costae, for example.

The pelvis object 104 is preferable to be formed by taking a line connecting the positions of the right and left iliac crests as a lateral reference line and a line connecting the position of the pubic symphysis and the position of the navel as a longitudinal reference line, and by translating each of the reference lines to fit the outer rim of the pelvis, for example. The right knee object 105a and the left knee object 305b are preferable to be formed to correspond to the positions and size of the knee joints (the center of the patella), for example.

The right foot object 106a and the left foot object 106b can be formed based on the entire outer rim of the foot, for example, and, specifically, are preferable to be formed based on a horizontal line passing the tip of the toe, a horizontal line passing the medial malleolus, a vertical line passing the medial malleolus, and a vertical line passing the outer edge of the metatarsophalangeal joint. The connecting lines 107 are a kind of object and connect the neighboring objects for visualizing the state and the like of the bones between the neighboring objects. The centroidal line 108 is preferable to be a line that passes the midpoint of a segment connecting the respective center points of the foot objects 106a and 106b, and is perpendicular to the floor face, for example.

Note that each of the objects is generated for making it easier to visually grasp the positions and inclinations of each body site. Therefore, even though without the objects are not generated, it is also possible to perform a posture assessment and an assessment of the muscle tone based on the reference points and reference lines used for generating the above-described objects. Further, the shapes of the objects are not limited to the square shape, round shape and stick shape shown in FIG. 9, but any shapes may be used as long as the positions and inclinations of each body site can be visually grasped therewith.

FIG. 3B is an example of display where prescribed objects are generated based on the posture image acquired by capturing the standing posture from the front, and the prescribed objects are superimposed on the posture image. On the posture image 111, shown are a head object 112, a thorax object 113, a pelvis object 114, knee objects 115, and foot objects 116 which are corresponding to prescribed sites of the body of the client. Further, a plurality of connecting lines 117 connecting each of the objects and a centroidal line 118 are shown on the posture image 111.

In FIG. 3B, each of the objects and the like is formed by using the method described in FIG. 3A. Each of the objects is preferable to be generated by the computer apparatus 1 by using a technique regarding conventionally known motion capture and a technique regarding image recognition, for example. When using the motion capture, each of the objects and the like can be generated by placing markers at the positions as the origins of the reference lines for generating each of the objects described above and detecting the positions of the markers, for example.

Further, at the time of capturing the image in step S1, it is also possible to display a reference image to be a reference for generating the objects such as the human skeleton chart shown in FIG. 3A on the display screen, for example, and capture the image by aligning the position of the body of the client with the reference image so as to display each of the objects generated based on the reference image while superimposing on the posture image.

When the positions and sizes of the generated objects and the like are inconsistent with those of the posture image, it is possible to receive input from the trainer or the client and adjust the positions, inclinations, and sizes of the objects and the like, for example.

When the image captured in step S1 is a video, that is, when the assessment target is a posture of the client in a moving state, it is preferable to generate the objects based on a still image acquired by temporarily stopping the video in a prescribed frame to be assessed. The object generating method may be the same method as described above or may be a method according to the criterion set for each motion. In view of increasing the accuracy of the assessment performed with the objects, motions performed in step S1 are preferable to be motions that include no changes in the shape of the spinal column and the body during the motions, such as flexion, extension, and rotation. However, the motions are not limited thereto. Examples of the motions that include no changes in the shape of the spinal column and the body during the motions, such as flexion, extension, and rotation, may be overhead squat, single-leg squat, and squat and hip rotation.

Figure 4:
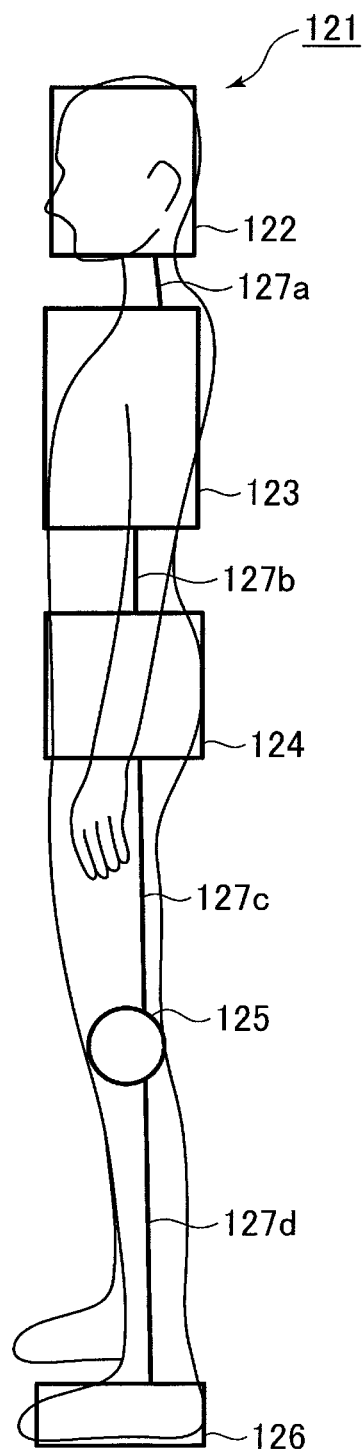
FIG. 4 is a schematic view regarding the object generating method corresponding to at least one of the embodiments of the present invention.

Next, by using FIG. 4, there is described an example of the object generating method in a case of using an image of the posture of the client captured from the left side (image of sagittal direction). FIG. 4 is a schematic view regarding the object generating method corresponding to at least one of the embodiments of the present invention. FIG. 4 shows an example of the object generating method when using an image of a state captured from the left side in which a client stands upright at a prescribed position such that each of the second toes of both feet faces the front while being parallel to each other, and looks straight at a designated article placed at a level of eyesight (standing position).

On a human body schematic chart 121, shown are a head object 122, a thorax object 123, a pelvis object 124, a knee object 125, and a foot object 126, which correspond to prescribed sites of the human body schematic chart. Further, a plurality of connecting lines 127a to 127d connecting each of the objects are shown on the human body schematic chart 121.

The head object 122 is preferable to be generated by taking a line connecting the positions of the eye and the external acoustic opening as a lateral reference line and a facial front line as a longitudinal reference line, and by translating each of the reference lines to fit the outer rim of the skull, for example.

The thorax object 123 is preferable to be generated by taking a line connecting the manubrium of sternum and the T3 spinous process as a lateral upper-side reference line, a line passing the lower margin of the 10th rib and parallel to the upper-side reference line as a lateral lower-side reference line, a line connecting the T3 spinous process to the T10 spinous process as a longitudinal right-side reference line, and a line passing the lower costal margin of the 10th rib and vertical to the upper-side reference line and the lower-side reference line as a longitudinal left-side reference line, for example.

The pelvis object 124 is preferable to be generated by taking a line passing the anterior superior iliac spine (ASIS) and the pubic symphysis in the front face of the pelvis as a longitudinal left-side reference line, a line connecting the anterior superior iliac spine and the posterior superior iliac spine (PSIS) as a lateral upper-side reference line, a line passing the pubic symphysis and parallel to the upper-side reference line as a lateral lower-side reference line, and a line passing the sacrum and parallel to the left-side reference line as a longitudinal right-side reference line, for example.

The knee object 125 is preferable to be generated to correspond to the position and size of the knee joint, for example. The foot object 126 is preferable to be generated based on the outer rim of the entire foot.

The connecting lines 127 are for connecting the objects neighboring to each other to visualize the state and the like of bone structures between the neighboring objects. For example, it is preferable for the connecting line 127*a* to be formed to correspond to the cervical vertebrae, the connecting line 127*b* to be formed to correspond to the lumbar vertebrae, the connecting line 127*c* to be formed to correspond to the femur, and the connecting line 127*d* to be formed to correspond to the shinbone. Although not shown, when a centroidal line is to be displayed, it is preferable to define a vertical line drawn from about 2 cm front of the lateral malleolus to the floor face as the centroidal line, for example.

Even in the case of using the image of the posture of the client captured from the side, it is possible to employ the configuration same as that of the case using the image of the posture of the client captured from the front except for the object generating method.

Returning to the flowchart of FIG. 2, the computer apparatus 1 assesses the positions and the like of the objects (step S4). In step S4, it is preferable to assess at least one or more out of the positions of each of the objects, inclinations, and the positional relationships between the neighboring objects, for example. Further, in view of performing a more accurate assessment on the posture of the client, it is more preferable to assess all of the positions of each of the objects, the inclinations, and the positional relationships between the neighboring objects.

It is preferable to assess the position of each of the objects based on the distance between the center of gravity of each of the objects such as the head object, the thorax object, the pelvis object, the knee objects, and the foot objects and the centroidal line, for example. It is preferable to assess the inclination of each of the objects based on whether or not the lateral lines configuring each of the objects are parallel to the floor face (whether or not the object is inclined either to the right or left), for example. When the distance between the center of gravity of the object and the centroidal line is zero or equal to or less than a prescribed distance, it is assessed that the position of the object is normal. Further, when the lateral lines configuring the object are substantially parallel to the floor face, it is assessed that the inclination of the object is normal.

It is preferable to assess the positional relationship between the neighboring objects based on how much shift there is in the distance between the prescribed references (for example, prescribed vertexes of the objects) of each of the objects, in the relation of the inclinations between each of the objects, and the like with respect to the case where the positions and the inclinations of each of the objects are normal.

The computer apparatus 1 determines the posture pattern of the client from the plurality of posture patterns set in advance based on the assessment result of the objects acquired in step S4 (step S5). In step S5, it is preferable to select a feature exhibited in the posture of the client from a plurality of feature candidates set in advance based on the assessment result of the objects acquired in step S4, and to determine the posture pattern based on the selected feature, for example.

Note that the posture pattern is classified based on types of the postures often observed in general in a prescribed steady state or moving state, for example. The posture pattern is preferable to be set for each type of assessment targets, such as front standing posture, side standing posture, front overhead squat posture, side overhead squat posture, and the like. Even though it is preferable to execute the processing regarding step S5 in view of enabling the client to grasp the body condition and in view of providing the exercise menu more suited for the client, the processing regarding step S5 may be omitted.

Note that the assessment of the positions and the like of the objects in step S4 and determination of the features and posture patterns in step S5 may be automatically performed by the computer apparatus 1 or may be performed by the trainer by assessing the positions and the like of the objects and inputting the feature observed in the posture of the client and the posture pattern thereof to the computer apparatus 1.

Figure 5:
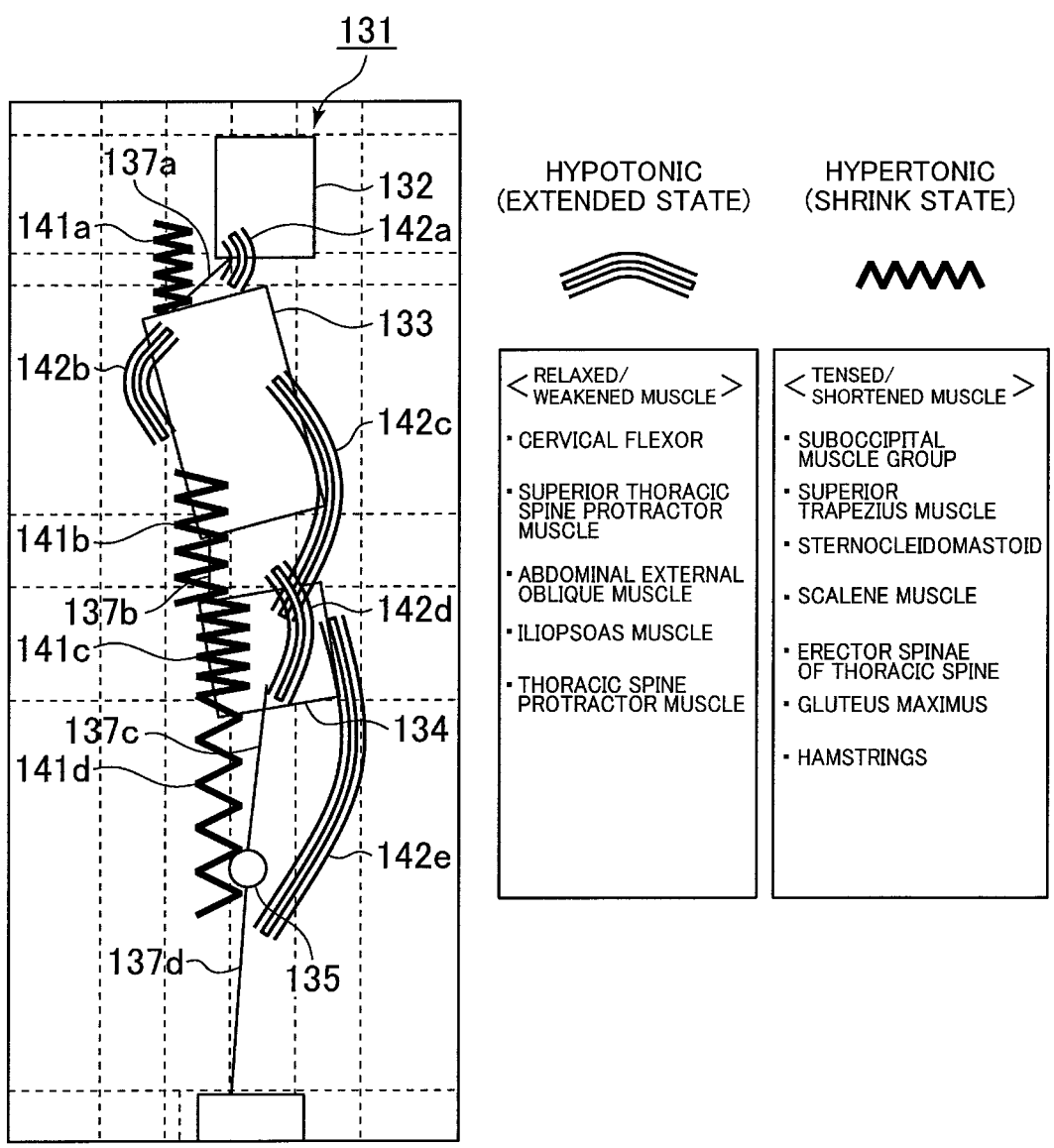
FIG. 5 is a schematic view regarding the assessment of the muscle tone corresponding to at least one of the embodiments of the present invention.

Then, the computer apparatus 1 surmises the muscle tone of the client based on the assessment result acquired in step S4 (step S6). Here, the processing performed in steps S4 to 6 will be described in detail. FIG. 5 is a schematic view regarding the assessment of the muscle tone corresponding to at least one of the embodiments of the present invention. In the example of FIG. 5, shown is the assessment of the muscle tone when using an object image generated based on the image acquired by capturing a standing posture from the right side.

An object image 131 is configured with a head object 132, a thorax object 133, a pelvis object 134, a knee object 135, a foot object 136, and a plurality of connecting lines 137*a* to 137*d*. Markers 141*a* to 141*d* show the positions of tensed muscles. Further, markers 142*a* to 142*e* show the positions of relaxed muscles. Note that specific examples of the tensed muscles shown by the markers 141*a* to 141*d* and the relaxed muscles shown by the markers 142*a* to 142*e* are illustrated in FIG. 5.

The muscle at the position corresponding to the marker 141*a* is surmised as a tensed muscle based on the fact that the acute angle formed between the connecting line 137*a* and the upper side of the thorax object 133 is smaller than the case where the positions and inclinations of each of the objects are normal, for example. Further, the muscle at the position corresponding to the marker 142*a* is surmised as a relaxed muscle based on the fact that the obtuse angle formed between the connecting line 137*a* and the lower side of the head object 132 is larger than that of the case where the positions and inclinations of each of the objects are normal, for example.

Moreover, the muscle at the position corresponding to the marker 142*c* is surmised as a relaxed muscle based on the fact that the distance of a route from the position of the midpoint of the right side of the thorax object 133 to the vertex at the upper right side of the pelvis object 134 via the right side of the thorax object 133 is longer than that of the case where the positions and inclinations of each of the objects are normal, for example.

Figure 6:
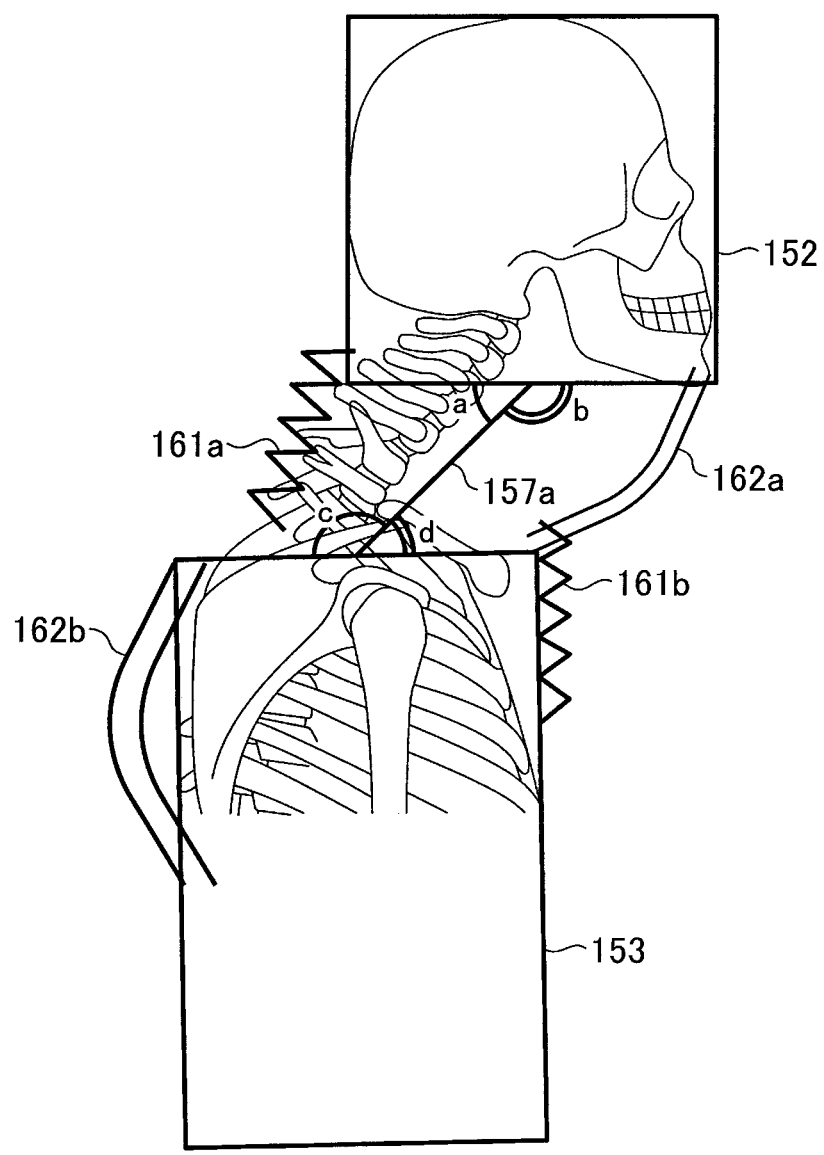
FIG. 6 is a schematic view regarding the assessment of the muscle tone corresponding to at least one of the embodiments of the present invention.
Figure 7:
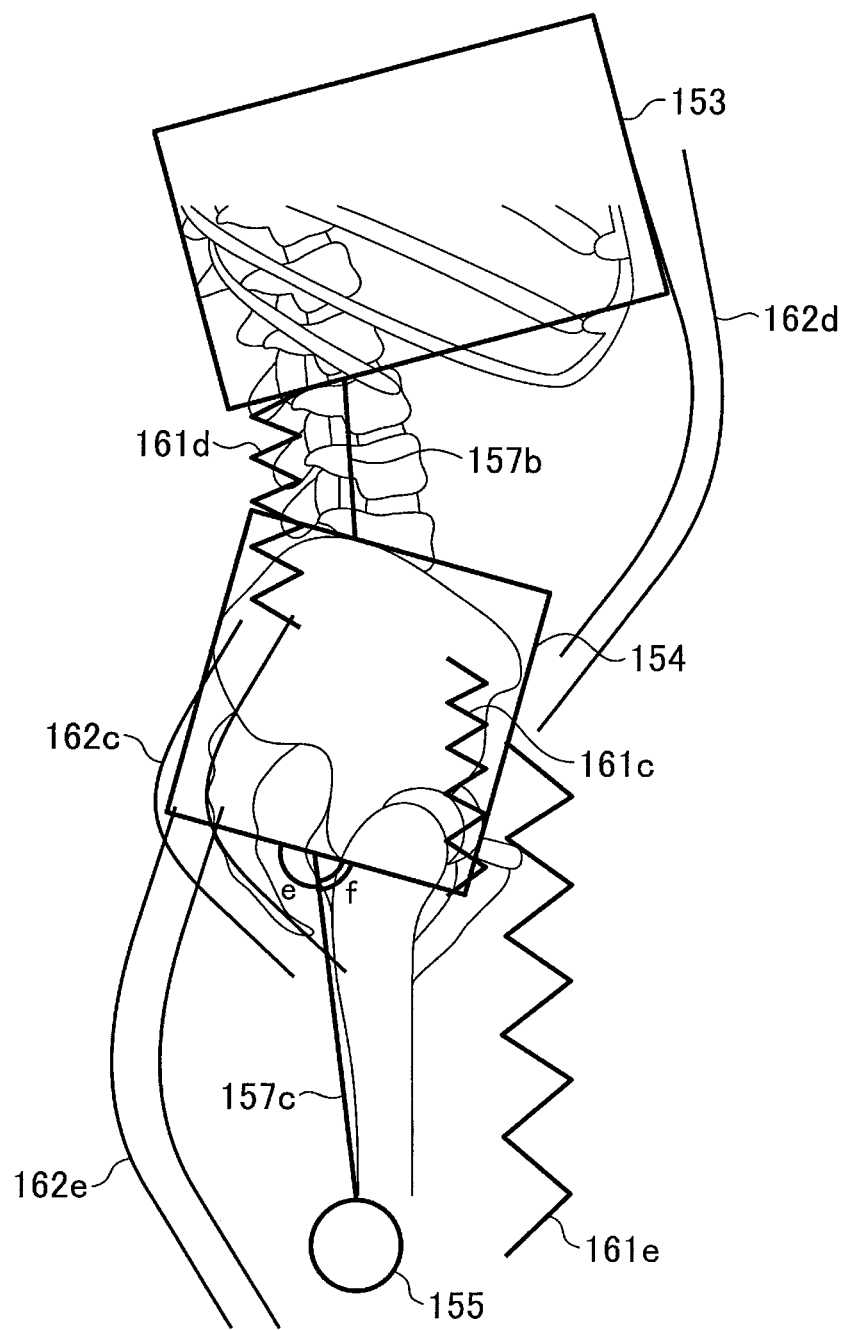
FIG. 7 is a schematic view regarding the assessment of the muscle tone corresponding to at least one of the embodiments of the present invention.

More specific examples of the assessment criteria of the muscle tone will be shown by using FIG. 6 and FIG. 7. FIG. 6 is a schematic view regarding the assessment of the muscle tone corresponding to at least one of the embodiments of the present invention, which in particular shows an example of the assessment of the muscle tone in the vicinity of the head to the thorax.

The muscle tone in the vicinity of the head to the neck can be assessed based on angles a and b formed between a connecting line 157*a* that connects a head object 152 and a thorax object 153 and the lower side of the head object 152, for example. The muscles at the position corresponding to a marker 161a (for example, the suboccipital muscle and upper fibers of the trapezius) are surmised as the tensed muscles based on the fact that the angle a is smaller than the angle (about 90 degrees) of a case where the positions and inclinations of each of the objects are normal. Further, the muscles at the position corresponding to a marker 162a (for example, the deep flexor muscle group of the neck) are surmised as the relaxed muscles based on the fact that the angle b is larger than the angle (about 90 degrees) of a case where the positions and inclinations of each of the objects are normal. Note that when the angle a is larger than 90 degrees, the muscles at the position corresponding to the marker 161a are surmised as the relaxed muscles. Similarly, when the angle b is smaller than 90 degrees, the muscles at the position corresponding to the marker 162a are surmised as the tensed muscles.

The muscle tone in the vicinity of the thorax can be assessed based on angles c and d formed between the connecting line 157a and the upper side of a thorax object 153, for example. The muscles at the position corresponding to a marker 162b (for example, middle fibers of the trapezius, lower fibers of the trapezius, and the serratus anterior muscle) are surmised as the relaxed muscles based on the fact that the angle c is larger than the angle (about 90 degrees) of a case where the positions and inclinations of each of the objects are normal. Further, the muscles at the position corresponding to a marker 161b (for example, the scalene muscle, the sternocleidomastoid, the pectoralis major muscle, and the pectoralis minor muscle) are surmised as the tensed muscles based on the fact that the angle d is smaller than the angle (about 90 degrees) of a case where the positions and inclinations of each of the objects are normal. Note that when the angle c is smaller than 90 degrees, the muscles at the position corresponding to the marker 162b are surmised as the tensed muscles. When the angle d is larger than 90 degrees, the muscles at the position corresponding to the marker 161b are surmised as the relaxed muscles.

FIG. 7 is a schematic view regarding the assessment of the muscle tone corresponding to at least one of the embodiments of the present invention, which in particular shows an example of the assessment of the muscle tone in the vicinity of the thorax to the pelvis.

The tone of the muscles located in the posterior and anterior of the pelvis can be assessed based on angles e and f formed between a connecting line 157c that connects a pelvis object 154 and a knee object 155 and the lower side of the pelvis object 154, for example. The muscles at the position corresponding to a marker 162c (for example, the gluteus medius, and the gluteus maximus) are surmised as the relaxed muscles based on the fact that the angle e is larger than the angle (about 90 degrees) of a case where the positions and inclinations of each of the objects are normal. Further, the muscles at the position corresponding to a marker 161c (for example, the iliac muscle, the psoas major muscle, and the psoas minor muscle) are surmised as the tensed muscles based on the fact that the angle f is smaller than the angle (about 90 degrees) of a case where the positions and inclinations of each of the objects are normal. Note that when the angle e is smaller than 90 degrees, the muscles at the position corresponding to the marker 162c are surmised as the tensed muscles. Similarly, when the angle f is larger than 90 degrees, the muscles at the position corresponding to the marker 161c are surmised as the relaxed muscles.

The tone of muscles located between the thorax object 153 and the pelvis object 154 and between the pelvis object 154 and the knee object 155 can be assessed based on the distance between each of the objects, for example. When the distance between prescribed vertexes of each of the objects is longer than a case where the positions and inclinations of each of the objects are normal (when the distance between the center of gravity of each of the objects and the centroidal line is equal to or shorter than a prescribed distance, and lateral lines configuring each of the objects are substantially parallel to the floor face, for example), the muscles located between the vertexes are surmised as the relaxed muscles. Further, when the distance between the prescribed vertexes of each of the objects is shorter than a case where the positions and inclinations of each of the objects are normal, the muscles located between the vertexes are surmised as the tensed muscles.

In the example of FIG. 7, the muscles at the position corresponding to a marker 162d (for example, the rectus abdominis muscle, and the abdominal oblique muscle) are surmised as the relaxed muscles based on the fact that the distance between the vertex at the lower right of the thorax object 153 and the vertex at the upper right of the pelvis object 154 is longer than a case where the positions and inclinations of each of the objects are normal. Similarly, the muscles at the position corresponding to a marker 161d (for example, the erector spinae muscle and the quadratus lumborum muscle) are surmised as the tensed muscles based on the fact that the distance between the vertex at the lower left of the thorax object 153 and the vertex at the upper left of the pelvis object 154 is shorter than a case where the positions and inclinations of each of the objects are normal.

Further, the muscles at the position corresponding to a marker 161e (for example, the rectus femoris muscle, and the psoas muscle) are surmised as the tensed muscles based on the fact that the distance between the vertex at the lower right of the pelvis object 154 and the intersection point between the knee object 155 and a connecting line 157c is shorter than a case where the positions and inclinations of each of the objects are normal. Similarly, the muscles at the position corresponding to a marker 162e (for example, the hamstrings) are surmised as the relaxed muscles based on the fact that the distance between the vertex at the lower left of the pelvis object 154 and the intersection point between the knee object 155 and a connecting line 157c is longer than a case where the positions and inclinations of each of the objects are normal.

As described above, it is possible to surmise the muscle tone by assessing prescribed muscle assessment items such as the angles formed between the objects, the connecting lines, and the like, the direct distance or the route distance between prescribed reference points on the objects and the connecting lines, for example, based on the prescribed muscle assessment criterion set for each of the muscle assessment items.

Further, it is also possible to surmise the level of hypertonia or hypotonia according to the size of the angle formed between the objects, the connecting lines, and the like, and the length of the direct distance, the route distance, or the like between the prescribed reference points on the objects and the connecting lines. For example, in FIG. 7, it can be surmised that the level of relaxation in the muscles at the position corresponding to the marker 162c is greater as the angle e becomes larger than the normal case. Similarly, it can be surmised that the level of tonus in the muscles at the position corresponding to the marker 161c is greater as the angle f becomes smaller than the normal case.

Further, in FIG. 7, for example, it can be surmised that the level of relaxation in the muscles at the position corresponding to the marker 162d is greater as the distance between the vertex at the lower right of the thorax object 153 and the vertex at the upper right of the pelvis object 154 becomes longer than the normal case. Similarly, it can be surmised that the level of tonus in the muscles at the position corresponding to the marker 161d is greater as the distance between the vertex at the lower left of the thorax object 153 and the vertex at the upper left of the pelvis object 154 becomes shorter than the normal case. By surmising the level of tonus or relaxation of the muscles, it is possible to make the exercise menu to be determined in step S7 to be described later more suited for the client. Further, based on the level of tonus or relaxation of the muscles, an appropriate priority order can be defined for the exercise menu to be determined in step S7 to be described later, for example.

Note that the surmise of the muscle tone in step S6 may be automatically performed by the computer apparatus 1 or may be performed by the trainer by assessing the prescribed muscle assessment items based on the prescribed muscle assessment criterion and inputting the information regarding the tensed muscles or the relaxed muscles to the computer apparatus 1. Further, it is also possible to associate each of the posture patterns with the surmised results of the muscle tone in each of the posture patterns and store those in advance. With such configuration, by simply determining the posture pattern of the client, for example, the surmised result of the muscle tone corresponding to such posture pattern can be acquired. Therefore, it is possible to lighten the processing load. In order to more accurately surmise the muscle tone, however, it is preferable to make assessment not from the posture patterns but from the positions of the objects, the inclinations of the objects, and the positional relationships among a plurality of objects based on the criterion described above.

Note that the muscle tone surmised in step S6 is preferable to be displayed on the display screen 19a and presented to the client by using the image as shown in FIG. 5 where the object image and the markers are integrally displayed. With such configuration, the client can easily grasp the own muscle tone, that is, the condition of the body.

Returning to the flowchart of FIG. 2, the computer apparatus 1 determines the exercise menu to be performed by the client based on the surmised result of the muscle tone acquired in step S6 (step S7), and ends the process. In step S7, for example, selected are an exercise menu for relaxing the muscles surmised as the tensed muscles in step S6 and an exercise menu for strengthening the muscles surmised as the relaxed muscles. Further, when the level of tonus or relaxation of the muscles is surmised in step S6, it is preferable to determine the priority and the number of execution times of the exercise included in the exercise menu according to such level. With such configuration, the exercise menu sufficiently suited for the client can be provided and, as a result, the probability of causing damages or general malaise by doing the exercise can be decreased.

Furthermore, in step S7, it is preferable to determine the exercise menu based further on the information regarding the client such as the chief complaint of the client and the purpose of the exercise in addition to the surmised result of the muscle tone acquired in step S6. With such configuration, it is possible to provide the exercise menu more suited for the client.

Here, the exercise menu includes at least one or more type of exercise. Further, the exercise menu is preferable to include the number of times the exercise is to be done. The information regarding the exercise menu determined in step S7 is displayed on the computer apparatus 1. The information regarding the exercise menu to be displayed is preferable to include an image showing how to do the exercise, the purpose of the exercise, and the priority of the exercise, for example, in addition to the name of the exercise, and the number of times the exercise to be performed. Such configuration makes it easier to enable the client to appropriately perform the most effective exercise. In addition, as a result of understanding and becoming conscious about the purpose of the exercise, the effect of the exercise can be increased further.

Further, while the client is performing the exercise menu determined in step S7, the state of exercising may be monitored by the sensor unit 16 or the like and, when the exercise is not being performed in an appropriate posture, it may be displayed so on the display screen 19a or may be outputted via voice from the sound output apparatus 15.

Second Embodiment

Next, outline of the second embodiment of the present invention will be described. Hereinafter, the second embodiment will be described by referring to a system that assesses the muscle tone of the client, which is implemented by a computer apparatus and a server apparatus that is connectable to the computer apparatus via communication.

Figure 8:
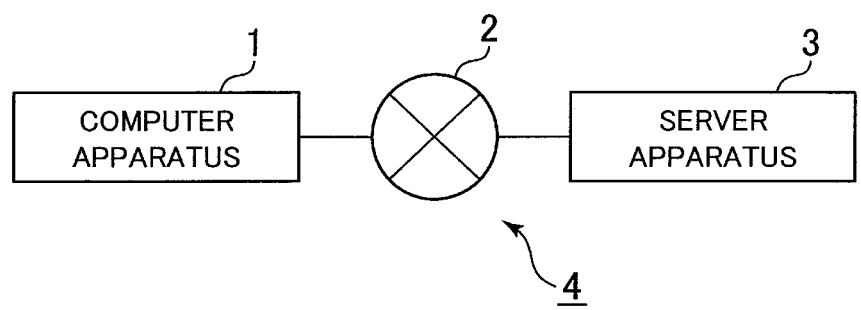
FIG. 8 is a block diagram illustrating the configuration of the system corresponding to at least one of the embodiments of the present invention.

FIG. 8 is a block diagram illustrating the configuration of the system corresponding to at least one of the embodiments of the present invention. As illustrated, a system 4 according to the embodiment is configured with the computer apparatus 1, the communication network 2, and the server apparatus 3.

The computer apparatus 1 is connected to the server apparatus 3 via the communication network 2. The server apparatus 3 may not have to be constantly connected to the computer apparatus 1 but may only need to be connectable as necessary.

For the specific configuration of the computer apparatus 1, the content described in the first embodiment may be employed within a necessary range. Further, the server apparatus 3 may be configured to include at least a controller, a RAM, a storage, and a communication interface, and to connect each of those via an internal bus.

Next, the configuration of the server apparatus 3 will be described. The controller is configured with a CPU and a ROM, and includes an internal timer for clocking the time. The controller executes programs stored in the storage and controls the server apparatus 3. The RAM is a work area of the controller. The storage is a memory area for saving the programs and data. The controller reads out the programs and data from the RAM and performs program execution processing based on the information and the like received from the computer apparatus 1.

The communication interface is capable of connecting to the communication network 2 wirelessly or with wire, and capable of transmitting/receiving data via the communication network 2. The data received via the communication network 2 is loaded on the RAM, and calculation processing is performed by the controller, for example.

Next, functions provided to the system according to the second embodiment will be described. The system 4 includes an image capturing function, an object generating function, an input receiving function, a posture assessing function, a muscle tone assessing function, an exercise menu determining function, a display function, and a storing function, for example. For each of the functions, the content described in the first embodiment may be employed within a necessary range.

While not specifically limited, it is preferable for the image capturing function, the input receiving function, and the display function, for example, to be provided to the computer apparatus 1 in the system according to the second embodiment. Furthermore, while not specifically limited, it is preferable for at least a part of the object generating function, the posture assessing function, the muscle tone assessing function, the exercise menu determining function, and the storing function, for example, to be provided to the server apparatus 3.

In the system according to the second embodiment, it is possible to employ the content described in the first embodiment for the flowchart of the program execution processing within a necessary range. While not specifically limited, it is preferable for the processing regarding step S1 and step S3, for example, to be executed mainly by the computer apparatus 1 and for the processing regarding other processing to be executed mainly by the server apparatus 3 in the second embodiment.

REFERENCE SIGNS LIST

1 Computer Apparatus
2 Communication Network
3 Server Apparatus
4 System
11 Controller
12 Ram
13 Storage
14 Sound Processor
15 Sound Output Apparatus
16 Sensor Unit
17 Frame Memory
18 Graphics Processor
19 Display Unit
20 Communication Interface
21 Interface Unit
22 Input Unit
23 Camera Unit

The invention claimed is:

1. A non-transitory computer-readable recording medium including a program causing a processor to execute assessment of muscle tone of a client, the program causing the processor to:
capture an image of a posture of the client in a steady state and/or an image of a posture of the client in a moving state;
assess the muscle tone of the client based on a position of a prescribed body site of the client, an inclination of the prescribed body site of the client, and/or positional relationships among a plurality of prescribed body sites in the captured image; and
assess whether the muscle tone of the prescribed body site of the client is in a tensed hypertonic state or in a relaxed hypotonic state,
wherein the program causing the processor to:
assess the muscle tone of the client located between a first prescribed body site and a second prescribed body site is in the tensed hypertonic state,
when a distance between a first prescribed point of the first prescribed body site or a second prescribed point of the second prescribed body site and a prescribed reference point on a connecting line connecting the first prescribed body site and the second prescribed body site is shorter than a distance in a case where positions and inclinations of each of the first and the second prescribed body sites are normal, or
when an acute angle formed between the connecting line and a first centroidal line of the first prescribed body site or a second centroidal line of the second prescribed body site is smaller than an acute angle in a case where positions and inclinations of each of the first and the second prescribed body sites are normal;
assess the muscle tone of the client located between the first prescribed body site and the second prescribed body site is in the relaxed hypotonic state,
when the distance between the first prescribed point of the first prescribed body site or the second prescribed point of the second prescribed body site and the prescribed reference point on the connecting line connecting the first prescribed, body site and the second prescribed body site is longer than the distance in a case where positions and inclinations of each of the first and the second prescribed body sites are normal, or
when the acute angle formed between the connecting line and the first centroidal line of the first prescribed body site or the second centroidal line of the second prescribed body site is larger than the acute angle in the case where positions and inclinations of each of first and second prescribed body sites are normal; and
apply the muscle tone assessment made by the processor to determine and display a candidate of an exercise menu suitable for the client to perform in order to reduce probability of causing damages or general malaise to the muscle of the client.

2. The non-transitory computer-readable recording medium according to claim 1, further causing the processor to generate a plurality of objects for visualizing the positions and/or the inclinations of each of the prescribed body sites of the client, wherein
the processor assesses the muscle tone of the client based on positions of the objects, inclinations of the objects, and positional relationships among the plurality of objects.

3. The non-transitory computer-readable recording medium according to claim 2, wherein the processor further assesses the muscle tone of the client based on a positional relationship between the objects neighboring to each other.

4. The non-transitory computer-readable recording medium according to claim 1, wherein the program further causing the processor to display the position of the muscle in the hypotonic state and/or the muscle in the hypertonic state in a prescribed mode.

5. An apparatus executing assessment of muscle tone of a client, comprising:
a camera that captures an image of a posture of the client in a steady state and/or an image of a posture of the client in a moving state; and
a processor that assesses the muscle tone of the client based on a position of a prescribed body site, an inclination of the prescribed body site, and/or positional relationships among a plurality of prescribed body sites in the image captured by the camera; and
assess whether the muscle tone of the prescribed body site is in a tensed hypertonic state or in a relaxed hypotonic state,
wherein the processor is configured to:

assess the muscle tone of the client located between a first prescribed body site and a second prescribed body site is in the tensed hypertonic state,
when a distance between a first prescribed point of the first prescribed body site or a second prescribed point of the second prescribed body site and a prescribed reference point on a connecting line connecting the first prescribed body site and the second prescribed body site is shorter than a distance in a case where positions and inclinations of each of the first and the second prescribed body sites are normal, or
when an acute angle formed between the connecting line and a first centroidal line of the first prescribed body site or a second centroidal line of the second prescribed body site is smaller than an acute angle in a case where positions and inclinations of each of the first and the second prescribed body sites are normal;
assess the muscle tone of the client located between the first prescribed body site and the second prescribed body site is in the relaxed hypotonic state,
when the distance between the first prescribed point of the first prescribed body site or the second prescribed point of the second prescribed body site and the prescribed reference point on the connecting line connecting the first prescribed body site and the second prescribed body site is longer than the distance in a case where positions and inclinations of each of the first and the second prescribed body sites are normal, or
when the acute angle formed between the connecting line and the first centroidal line of the first prescribed body site or the second centroidal line of the second prescribed body site is larger than the acute angle in the case where positions and inclinations of each of first and second prescribed body sites are normal; and
apply the muscle tone assessment made by the processor to determine and display a candidate of an exercise menu suitable for the client to perform in order to reduce probability of causing damages or general malaise to the muscle of the client.

6. A muscle tone assessment method for assessing muscle tone of a client, comprising:
capturing an image of a posture of the client in a steady state and/or an image of a posture of the client in a moving state;
assessing the muscle tone of the client based on a position of a prescribed body site of the client, an inclination of the prescribed body site of the client, and/or positional relationships among a plurality of prescribed body sites in the captured image; and
assessing whether the muscle tone of the prescribed body site of the client is in a tensed hypertonic state or in a relaxed hypotonic state,
wherein the method further comprising:
assessing the muscle tone of the client located between a first prescribed body site and a second prescribed body site is in the tensed hypertonic state,
when a distance between a first prescribed point of the first prescribed body site or a second prescribed point of the second prescribed body site and a prescribed reference point on a connecting line connecting the first prescribed body site and the second prescribed body site is shorter than a distance in a case where positions and inclinations of each of the first and the second prescribed body sites are normal, or
when an acute angle formed between the connecting line and a first centroidal line of the first prescribed body site or a second centroidal line of the second prescribed body site is smaller than an acute angle in a case where positions and inclinations of each of the first and the second prescribed body sites are normal;
assessing the muscle tone of the client located between the first prescribed body site and the second prescribed body site is in the relaxed hypotonic state,
when the distance between the first prescribed point of the first prescribed body site or the second prescribed point of the second prescribed body site and the prescribed reference point on the connecting line connecting the first prescribed body site and the second prescribed body site is longer than the distance in a case where positions and inclinations of each of the first and the second prescribed body sites are normal, or
when the acute angle formed between the connecting line and the first centroidal line of the first prescribed body site or the second centroidal line of the second prescribed body site is larger than the acute angle in the case where positions and inclinations of each of first and second prescribed body sites are normal; and
applying the muscle tone assessment to determine and display a candidate of an exercise menu suitable for the client to perform in order to reduce probability of causing damages or general malaise to the muscle of the client.

7. A system for assessing muscle tone of a client, the system comprising:
a processor; and
a memory operatively connected to the processor via a communication interface, the memory storing computer readable instructions, when executed, cause the processor to:
capture an image of a posture of the client in a steady state and/or an image of a posture of the client in a moving state; and
assess the muscle tone of the client based on a position of a prescribed body site, an inclination of the prescribed body site, and/or positional relationships among a plurality of prescribed body sites in the captured image; and
assess whether the muscle tone of the prescribed body site is in a tensed hypertonic state or in a relaxed hypotonic state,
wherein the computer readable instructions, when executed, further cause the processor to:
assess the muscle tone of the client located between a first prescribed body site and a second prescribed body site is in the tensed hypertonic state,
when a distance between a first prescribed point of the first prescribed body site or a second prescribed point of the second prescribed body site and a prescribed reference point on a connecting line connecting the first prescribed body site and the second prescribed body site is shorter than a distance in a case where positions and inclinations of each of the first and the second prescribed body sites are normal, or
when an acute angle formed between the connecting line and a first centroidal line of the first prescribed body site or a second centroidal line of the second prescribed body site is smaller than an acute angle in a case there positions and inclinations of each of the first and the second prescribed body sites are normal;

assess the muscle tone of the client located between the first prescribed body site and the second prescribed body site is in the relaxed hypotonic state,
- when the distance between the first prescribed point of the first prescribed body site or the second prescribed point of the second prescribed body site and the prescribed reference point on the connecting line connecting the first prescribed body site and the second prescribed body site is longer than the distance in a case where positions and inclinations of each of the first and the second prescribed body sites are normal, or
- when the acute angle formed between the connecting line and the first centroidal lire of the first prescribed body site or the second centroidal line of the second prescribed body site is larger than the acute angle in the case where positions and inclinations of each of first and second prescribed body sites are normal; and apply the muscle tone assessment made by the processor to determine and display a candidate of an exercise menu suitable for the client to perform in order to reduce probability of causing damages or general malaise to the muscle of the client.

\* \* \* \* \*

UNITED STATES PATENT AND TRADEMARK OFFICE
CERTIFICATE OF CORRECTION

PATENT NO.          : 11,744,483 B2
APPLICATION NO.     : 16/627490
DATED               : September 5, 2023
INVENTOR(S)         : R. Takagi et al.

Page 1 of 1

It is certified that error appears in the above-identified patent and that said Letters Patent is hereby corrected as shown below:

In the Claims

Column 20, Line 66 (Claim 7, Line 36) please change "case there" to -- case where --

Signed and Sealed this
Second Day of January, 2024

Katherine Kelly Vidal
*Director of the United States Patent and Trademark Office*